United States Patent
Dolleris

(10) Patent No.: US 8,092,447 B2
(45) Date of Patent: Jan. 10, 2012

(54) HANDPIECE FOR TISSUE TREATMENT

(75) Inventor: Casper Dolleris, Vancouver (CA)

(73) Assignee: Asah Medico A/S, Hvidovre (DK)

( * ) Notice: Subject to any disclaimer, the term of this patent is extended or adjusted under 35 U.S.C. 154(b) by 1776 days.

(21) Appl. No.: 10/521,030

(22) PCT Filed: Jul. 11, 2003

(86) PCT No.: PCT/DK03/00489
§ 371 (c)(1),
(2), (4) Date: Sep. 29, 2005

(87) PCT Pub. No.: WO2004/007022
PCT Pub. Date: Jan. 22, 2004

(65) Prior Publication Data
US 2006/0116669 A1     Jun. 1, 2006

Related U.S. Application Data

(60) Provisional application No. 60/394,859, filed on Jul. 11, 2002.

(51) Int. Cl.
*A61B 18/18* (2006.01)
(52) U.S. Cl. .............. 606/13; 606/9; 606/10; 607/88; 607/91
(58) Field of Classification Search .......... 606/9–19; 607/88–91, 93; 128/898
See application file for complete search history.

(56) References Cited

U.S. PATENT DOCUMENTS

| | | | |
|---|---|---|---|
| 4,576,160 A * | 3/1986 | Tanaka | 606/10 |
| 5,312,397 A | 5/1994 | Cosmescu | |
| 6,074,382 A | 6/2000 | Asah et al. | |
| 6,325,794 B1 | 12/2001 | Yoon et al. | |
| 6,356,366 B1 | 3/2002 | Popovich | |
| 6,383,177 B1 * | 5/2002 | Balle-Petersen et al. | 606/9 |

FOREIGN PATENT DOCUMENTS

DE    41 30 591 A1    3/1993
WO    WO 00/07496    2/2000

* cited by examiner

*Primary Examiner* — Ahmed Farah
(74) *Attorney, Agent, or Firm* — Merchant & Gould P.C.

(57) ABSTRACT

A handpiece for tissue treatment is provided. The handpiece has receiving means for receiving a first light beam, at least two components and selector device being movable between at least two positions, each position corresponding to a component. The selector device may be moved between the two positions, thereby positioning a selected component in a beam path of the first light beam. The selected component provide one or more functions, such as sensing, emitting a third light beam, emitting no light beam, and/or emitting a second light beam in response to the first light beam being incident on the selected component. The second or third light beam may, if present, be emitted towards a target area, or said light beam(s) may be deflected towards a target area. Furthermore, a method for tissue treatment using such a handpiece, and a selector device for use in such a handpiece is provided.

22 Claims, 8 Drawing Sheets

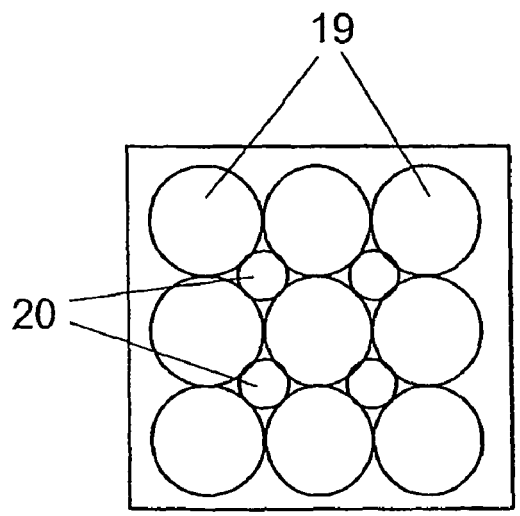
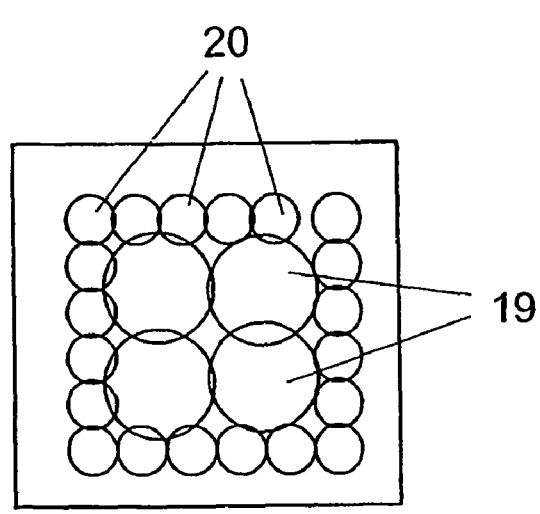
Fig. 5A  Fig. 5B
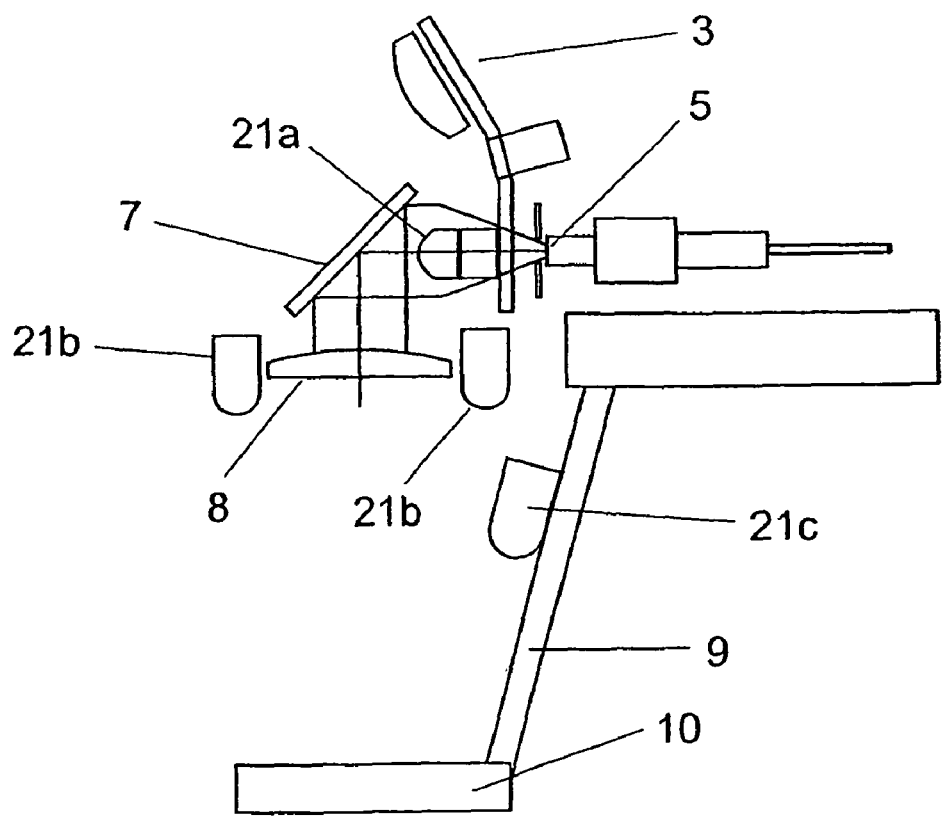
Fig. 6

HANDPIECE FOR TISSUE TREATMENT

TECHNICAL FIELD

The present invention relates to a handpiece for tissue treatment using a light source, the handpiece having a selector device. Furthermore, the present invention relates to a method for tissue treatment using such a handpiece, and to a selector device for use in such a handpiece.

BACKGROUND OF THE INVENTION

It is known to use a handpiece, e.g. in combination with a scanning device, for tissue treatment, such as described in U.S. Pat. No. 6,190,376, U.S. Pat. No. 6,074,382, and in U.S. Pat. No. 6,383,177 hereby incorporated by reference. However, in known handpieces the components constituting the handpiece, such as optical components, are 'fixed', i.e. they are impossible or at least very difficult to exchange for other components. Therefore, the known handpieces are designed for specific purposes or specific kinds of treatment, and/or to be used in combination with specific light sources. Thus, they are relatively inflexible and not easily adapted to other purposes or light sources than those they were originally designed to.

SUMMARY OF THE INVENTION

It is an object of the present invention to provide a handpiece, which is very flexible and easily adapted to a desired purpose and/or light source.

It is a further object of the present invention to provide a handpiece in which a component may easily be exchanged or replaced.

It is an even further object of the present invention to provide a method for tissue treatment by means of a handpiece according to the present invention.

It is a still further object of the present invention to provide a method for tissue diagnosis.

The above and other objects are obtained by the present invention, which according to a first aspect provides a handpiece comprising:
  means for receiving a first light beam emitted from a first light source,
  at least two components,
  a selector device being movable between at least two positions, each position corresponding to a component,
  means for moving the selector device between said at least two positions, thereby positioning a selected component in a beam path of the first light beam, the selected component providing one or more functions.

The selected component may be adapted to sense, to emit a third light beam, to emit no light beam and/or to emit a second light beam in response to the first light beam being incident on the selected component, so that the functions may be selected from the group consisting of sensing, emitting a third light beam, emitting no light beam, and emitting a second light beam in response to the first light beam being incident on the selected component.

The second or third light beam may, if present, be emitted towards a target area or wherein the handpiece further comprises deflecting means for deflecting the second or third light beam, if present, towards a target area.

According to a second aspect of the present invention, a selector device for a handpiece is provided, the selector device being movable between at least two positions, each position corresponding to positioning a component in a beam path of a first light beam, a component being selected when the selector device is moved to the position corresponding to that component, the selected component providing one or more specific functions.

The one or more specific functions may be selected from a group consisting of sensing, emitting a third light beam, emitting no light beam, and/or emitting a second light beam in response to the first light beam being incident on the selected component.

The selector device may advantageously be positioned in a handpiece according to the invention, thereby providing a very flexible handpiece in which a desired component may easily be positioned in the beam path of the first light beam.

Preferably, the selector device is positioned entirely within the handpiece. It is an advantage that no additional openings are introduced into the handpiece so as to prevent dust and dirt from interfering with the optics of the handpiece. Alternatively, one or more parts of the selector device may project from the handpiece. Hereby, more components and/or larger selector devices may be used.

According to a third aspect of the present invention, there is provided a method for tissue treatment and/or cosmetic treatment of tissue by means of a handpiece comprising at least two components and a selector device being movable between at least two positions, each position corresponding to a component, the method comprising the steps of:
  receiving a first light beam emitted from a first fight source,
  moving the selector device to a predetermined position, so as to move the corresponding component into a beam path of the first light beam, thereby selecting said corresponding component,
  sensing, emitting a third light beam, emitting no light beam, or emitting a second light beam in response to the first light beam being incident on the selected component, by means of the selected component,
  deflecting or emitting the second or third light beam, if present, towards a target area on the tissue to be treated.

According to a fourth aspect of the present invention, there is provided a method for tissue diagnosis of tissue at a target area by means of a handpiece comprising at least two components and a selector device being movable between at least two positions, each position corresponding to a component, the method comprising the steps of:
  illuminating the target area,
  deflecting light reflected from the target area onto a predetermined position,
  obtaining information about the target area by moving the selector device to the predetermined position, so as to move a first component into a beam path of the light reflected from the target area.

It is an advantage of providing a method for tissue diagnosis that the handpiece may be very flexible and provide a detailed diagnosis of a tissue so that an optimum treatment of the tissue at the target area may be selected. The treatment may be a treatment according to the third aspect of the invention or it may be another suitable treatment, the other treatment obtaining information from the handpiece.

The first light source may comprise a coherent light source, such as a laser device, such as a $CO_2$ laser, a YAG laser, such as an Erbium YAG laser, a Holmium YAG lasers, a Nd YAG laser, etc., a semiconductor laser, such as a laser diode, a pulsed laser, a gas laser, a solid state laser, a Hg laser, an excimer laser, an Optical Parametric Oscillator (OPO) laser, a metal vapour laser, etc. Alternatively, the first light source may be a non-coherent light source, such as a lamp, a light bulb, a flash lamp, etc.

It is, however, envisaged that other electromagnetic wave sources than light sources may be used in a handpiece according to the invention. An electromagnetic wave source for emission of X-ray waves, microwaves, etc. may be equally applied. Even though the term light source is used throughout the description, the principles apply generally to all electromagnetic wave sources with the at least two components of the selector device as well as other components, such as the deflecting means, of the handpiece being adapted to the specific wavelength of the electromagnetic wave source. It is preferred to adapt the components to the specific wavelength of the electromagnetic wave source used, irrespective of the wavelength of the waves emitted from the electromagnetic wave source. The electromagnetic wave source may emit waves having a wavelength in the infrared part of the electromagnetic spectrum, such as in a wavelength range from 0.75 µm to 100 µm, such as in a near infrared part of the spectrum, such as from 0.75 µm to 1.5 µm, such as in a middle infrared part of the spectrum, such as from 1.5 µm to 30 µm, such as in a far infrared part of the spectrum, such as from 30 µm to 100 µm, in the visible part of the electromagnetic spectrum, such as in a wavelength range from 0.390 µm to 0.770 µm, and in the ultraviolet part of the electromagnetic spectrum, such as from 10 nm to 390 nm, such as in the near ultraviolet part of the spectrum, such as from 300 nm to 390 nm, such as in the far ultraviolet part of the spectrum, such as from 200 nm-300, such as in the extreme ultraviolet part of the spectrum such as from 10 nm to 200 nm. The electromagnetic wave source may further emit X-rays, such as x-rays in a frequency range from $10^{16}$ Hz-$10^{22}$ Hz, or microwaves, such as microwaves in a frequency range from $10^8$ Hz-$10^{11}$ Hz.

Presently, lasers are a preferred light source and the light beam emitted from the laser is preferably coupled into an optical fiber delivering the light beam to the handpiece.

Present $CO_2$ lasers emit light at a wavelength of 10600 nm. The $CO_2$ laser is particularly well suited as a light source in an apparatus for ablating dermal cells as water has a high energy absorbance at 10600 nm and the $CO_2$ laser is capable of reliably delivering the required laser power.

Erbium YAG lasers emit light at a wavelength of 2930 nm. Water absorbs less energy at this wavelength that at 10600 nm. Therefore, the Erbium YAG laser may be preferred for ablating thinner layers of dermal cells than may be ablated with a $CO_2$ laser. Tissue having been treated with light emitted from an Erbium YAG laser may heal faster than tissue having been treated with $CO_2$ laser light as a thinner layer of dermal cells is influenced by Erbium YAG laser light. An Erbium YAG laser may also be preferred when photocoagulation of blood vessels is to be avoided.

A CO laser emits light in the 4500 nm to 5500 nm wavelength range. Water absorption at these wavelengths is somewhat less than water absorption at 10600 nm. A CO laser light source is presently preferred for dental treatment, e.g. for removal of carries, as dentine is not influenced by illumination of light from a CO laser.

A Nd Yag laser emits light at a wavelength of 1060 nm and is well suited for hair epilation by selective photo thermolysis, since light at this wavelength causes local heating of the hair bulb due to absorption of the light in the oxyhemoglobin contained in the capillaries.

A Nd YAG laser with a frequency doubled output beam in the 520-680 nm wavelength range is presently preferred as a light source for treatment of hypervasculation. Light in this wavelength range causes photocoagulation of blood without affecting surrounding tissue provided that an appropriate intensity of the light beam is directed towards the micro vessels for an appropriate period of time. Coagulation stops blood flow in the treated vessels whereby discoloration of the skin also stops.

A solid state diode laser emitting a wavelength of 810 nm is presently preferred for hair epilation by selective photothermolysis as this wavelength is absorbed by the melanin contained in the hair shaft. The hair bulb is thus damaged due to heat transportation through the hair shaft.

Typically, a power density greater than about 50 W/mm$^2$, such as a power density in the range from about 50 W/mm$^2$ to about 180 W/mm$^2$, is adequate for vaporizing cells with a minimum of damage to the surrounding tissue.

Generally, the power density is adapted to the wavelength and the tissue to be treated.

The deflecting means may comprise any optical component or components suitable for deflecting light emitted from the first light source, such as mirrors, prisms, diffractive optical elements, such as holograms, grids, gratings, etc.

The deflecting means are preferably movably mounted for displacement of the deflecting means as a function of time, so that the light beam emitted from the handpiece, i.e. the second or third light beam, may traverse a target area along a desired curve while the handpiece is kept in a fixed position. Preferably, the deflecting means are rotatably mounted, and the actual deflection of the light beam is determined by the current angular position of the deflecting means.

Deflecting moving means, such as actuators, such as piezo electric crystals, may be utilised to control positions of the deflecting means, the displacement of the deflecting means is controlled by applying a specific electric voltage to electrodes of the deflecting moving means. The deflecting moving means may comprise electromotors generating linear or rotational displacements, galvanometers, magnetically activated or controlled actuators, pneumatic actuators, hydraulic actuators, etc.

The positions of the deflecting means may be controlled by deflecting control means adapted to control the deflecting moving means so that the deflecting means deflect the light beam in such a way that the light beam traverses a target area along a desired curve or in a predetermined pattern, (see for example U.S. Pat. No. 6,190,376).

The deflecting means may for example comprise two mirrors for deflecting of the light beam in two dimensions, and the deflecting moving means for the mirrors may be constituted by electromotors, e.g. each mirror may be directly connected to a shaft of a corresponding motor, whereby each motor is used for angular positioning of the corresponding mirror. Alternatively, the deflecting means may comprise a single mirror being able to move independently in two directions. The mirror may then be positioned facing downwards, thus reducing the amount of dust on the mirror surfaces since dust will not naturally settle on a mirror surface facing downwards.

When the handpiece is kept in a fixed position in relation to a target area, and is emitting a second or third light beam towards the target area, changing of the position of the deflecting means causes the second or third light beam to traverse or scan the target area along a curve. An area may be traversed or scanned by the second or third light beam, e.g. by letting the second or third light beam traverse or scan a meander like curve substantially covering the area or, by traversing or scanning the area line by line. In the present context, the type, number and shape of curves traversed by the second or third light beam in order to traverse a specific area are denoted the traversing pattern or the scan pattern. The area that is scanned or traversed by the second or third light beam is denoted the scan area, the treatment area or the traversed area.

A light source for providing a visible aiming light beam may be provided, either in the handpiece or in combination with the first light source and be provided to the handpiece via a fiber. The aiming light beam may be adapted to be traversed around at least a part of the circumference of the target area thereby indicating the size, shape and position of the target area to be traversed with the second or third light beam. When a polygonal shape of the target area has been selected, the visible light beam may, e.g. between traversing by the treating light beam, be traversed along one edge of the polygon. The aiming light beam is of particular interest when the second or third light beam is invisible. The aiming light beam may then assist the operator by indicating areas towards which the invisible light beam is directed during traversing. A second light source may provide the aiming beam.

A handpiece is a single unit for conveniently holding in one hand by an operator of the handpiece.

The selector device may comprise an at least substantially circular disc or plate, in which case the means for moving the selector device comprises means for rotating the disc about an axis of symmetry of the disc. In this embodiment, the at least two components may be arranged annularly along the edge of the disc, and a specific component may be selected when a portion of the disc comprising that component is rotated into the path of the first light beam. Thus, the disc is preferably positioned with at least part of the edge region in the beam path, such that when the disc is rotated the components are consecutively positioned in the beam path. The rotation may be stopped when a desired component is positioned in the beam path, the component thereby being selected.

Alternatively, the selector device may comprise an elongated plate, in which case the means for moving the selector device comprises means for moving the plate at least substantially linearly along a longitudinal axis of the elongated plate. In this embodiment the at least two components may be arranged along a longitudinal axis of the plate, and a specific component may be selected when a portion of the elongated plate comprising that component is moved linearly into the path of the first light beam. This is similar to the embodiment described above, except that in this case the components are arranged in a row and the plate is moved at least substantially linearly, e.g. sideways or in an up/down direction. The plate is preferably positioned in the beam path in such a way that when it is moved substantially linearly along the longitudinal axis of the plate, the components are consecutively positioned in the beam path. As described above, a component may be selected by stopping the movement when that component is positioned in the beam path of the first light beam.

It is envisaged that the selector device may have any form suitable to be positioned in the handpiece so that the at least two components in turn may be positioned in the beam path of the first light beam. The selector device itself may for example be provided with impressions, indentations, etc. to allow for positioning of the at least two components, so as to for example ease mounting of components having different sizes and shapes, etc.

The selector device may have a size, which is capable of supporting the desired components, and at the same time have a size so that it may be positioned within the handpiece. For a selector device comprising a circular disc, the diameter of the disc may be 25-50 mm, such as 30-40 mm, such as preferably 36-40 mm. For a selector device comprising an elongated plate, the plate may be 25-60 mm long. The handpiece may be provided with 'bumps' of finger-holds on the outside to make room for the selector device in the inside of the handpiece.

The selector device may be mounted in the apparatus or the handpiece so that an exchange or an replacement of the selector device may be performed by e.g. an operator of the apparatus or, alternatively, by a technician performing maintenance of such apparatuses. Hereby, the components may be exchanged by other components, either in case of a broken component or if another treatment make use of other components. A number of pre-mounted selector devices may; thus, be provided with the apparatus or handpiece. A corresponding software package may accompany the selector device or, alternatively, be pre-installed in the handpiece, such as in an electronic memory, such as an EEPROM, of the handpiece.

The means for moving is, preferably, electrically controlled so that a user selection of a desired component causes a signal to be sent to the moving means whereby the moving means are controlled to move the selector device so that the desired component is positioned in the beam path of the first light beam. Alternatively, the means for moving the selector device may be mechanical means, so that the selector device may be moved e.g. by rolling a knob, turning a wheel, for example by turning a projecting part of the selector device, etc.

It is an advantage, that the means for moving may be controlled electrically so that the selector device may be changed by a command from the first light source, or may be controlled according to a pre-programmed software.

Furthermore, the change of components may be performed quietly, which has a significant impact on the comfort experienced by a user or operator of the handplece as well as a patient being treated. The moving means may, furthermore, be adapted to position the components very fast, accurate and with a high repeatability. The components may, for example, be positioned with a repeatability better than 500 μm, such as better than 100 μm, such as better than 50 μm. It is an advantage of the accurate positioning of the components that the optical losses due to misalignment of the components are minimized. The positioning time for the components may be in the range of 10-500 ms, such as 10-200 ms, such as 50-200 ms, such as 100-200 ms, preferably such as 150 ms, e.g. for half a turn of a circular disc in the selector device. The positioning time or the positioning speed may be software controlled so that the overall impact on the handpiece may be varied, that is the noise, the power consumption, the mechanical wear, the mechanical shake, etc.

By controlling the positioning time, the mentioned parameters may, thus, be tailored according to the actual application. By, e.g., lowering the speed or the positioning time in non-critical applications, an even quieter movement may be achieved. The selector device and the means for moving may, preferably, be manufactured so that the mechanical function is very stable whereby minimizing the mechanical shake.

The selector device is preferably inserted in the beam path between the receiving means for receiving the first light beam and the deflecting means.

At least one of the at least two components may preferably be an optical component, such as an optical lens, a reflective mirror, a prism, a diffractive optical element, such as a hologram, a grid, a grating, etc.

In case at least one of the components is an optical lens, a spot of a size determined by the optical lens selected illuminates the target area. In this embodiment at least two of the optical components may be optical lenses so that the spot size at the target area may be varied by selecting optical lenses having varied optical parameters and being positioned at the selector device so that the distance from the lens to the deflecting means varies correspondingly. This provides a very flexible handpiece wherein the spot size may easily be selected according to a specific purpose or patient. Furthermore, the spot size may be changed during a treatment session, e.g. in order to provide a very homogeneous treatment and/or in order to avoid unnecessary overlap between treated areas and/or in order to avoid untreated areas. The spot size may be varied from 0.1 mm to 20 mm, such as from 0.1 mm to 10 mm, such as from 1 mm-10 mm, etc. The spot size is given as the diameter of a circular spot size. It is however envisaged that the size of any polygonal shaped spot may be given by the diameter of a corresponding circumscribed circle.

It is an advantage that the spot size at the target area may be determined by simply changing the lens at the selector device without changing any other parts of the deflecting means and without changing any output lenses of the handpiece.

In case at least one of the components is a diffractive element, the element may be used, e.g. in combination with a second light source, so that a predetermined pattern, preferably the predetermined pattern in which to traverse the target area, or a circumference of the predetermined pattern, is shown on the target area. Furthermore, a diffractive optical element may be used, e.g. in combination with a lens, as a beam transforming element so as to provide for spots on the target area having any arbitrary shape, such as polygonal, such as rectangular, quadratic, triangular, etc, or circular, elliptic, etc. It is hereby possible to design e.g. a pattern having substantially no areas which are not treated.

Furthermore, at least one of the at least two components may be a sensor or a detector providing information about the target area. The information provided may for example comprise information about tissue parameters, such as colour, temperature, texture, elasticity, size, shape, reflectivity, and scattering properties, etc. Tissue may hereafter be classified into specific tissue conditions, such as tissue types, skin disorders, cutaneous damage, etc., according to predetermined values of the various tissue parameters or by values of mathematical functions of such parameters. Further, the functions may include averages, weighted averages, correlations, cross-correlations, etc, of mathematical functions.

Such tissue conditions may comprise any cutaneous damage, skin disorder or skin irregularity, such as wrinkles, small marks on the tissue, such as marks from chloasma, liver spots, red spots, tattoos, blood vessels, beauty spots, freckles, etc., as well as warts, wounds, moles, hair follicles, tumours, etc., as well as tissue types of the target area, such as very light skin, light skin, dark skin, darker skin, etc. The handpiece according to the invention may be used for removing skin disorders by ablation, removing vascular disorders by vessel coagulation, wrinkle removal by subcutaneous collagen denaturation, etc. Furthermore, the handpiece of the invention may be used for tissue stimulation, for therapeutic purposes, such as reduction of pain, such as reduction of inflammation, reduction of erythema, promotion of processes of photobiostimulation, etc. Hereafter, the terms tissue and resurfacing and treatment will include these marks and treatments thereof, and treatment will further include tissue stimulation and therapeutic use.

For example, various marks may be detected by their colour. Thus, the detector means may comprise light detectors for detection of intensity of light emitted from tissue at the target area, the target area being the area to be treated by the first light beam or being the area the handpiece is currently directed at.

Certain tissue conditions, such as small marks on the tissue such as marks from chloasma, liver spots, red spots, tattoos, blood vessels, beauty spots, freckles, etc, to be treated may be characterised by the shape or the size of the area covered by the tissue condition in question. For example, when treating different types of marks of substantially identical colours, it may be desirable to treat each type of mark differently and according to the respective size or shape of the type of marks in question.

When removing hairs, it is important to identify the type of tissue on which the hairs are to be removed in order to specifically customise the hair removal towards the tissue type in question and the corresponding colour of the hairs to be removed.

The sensor may be a camera, such as a video camera, such as a charged-coupled device (CCD) camera, or a complementary metal-oxide semiconductor (CMOS) camera. The sensor may, furthermore, be a detector, such as a wavelength sensitive detector, an intensity sensitive detector, etc. The sensor may be one or more array(s) of sensors or it may be a single sensor or detector, sensing information from one position or one pixel at a time, thus collecting information of at least part(s) of the target area during scanning of the target area so that reflected light from at least a part of the target area reaches the sensor during scanning of the target area.

Still further, another of the at least two components may comprise another sensor providing further information about the target area and the tissue at the target area. Different sensors may for example be sensitive to reflected light in different wavelength ranges, or a number of sensors may be applied so that the combined field of view for the number of sensors encompass the target area. Especially when using sensors having a high resolution, the field of view of a single sensor may not be able to encompass the entire target area. A number of different sensors may e.g. be combined at a single component or a single component position on the selector device.

The camera may be connected to a display or a monitor and thus be used as a microscope for enlarging at least part(s) of the target area. Furthermore, the display may show illumination by non-visible light sources, such as an image of ultraviolet illumination, such as an image of infra-red illumination, etc. Still further, the display may trace the treating or second light source and, thus, display the treating light beam or another light beam, such as a third light beam, during traversing of the target area.

The sensor may be adapted to provide an image of the target area before, during and/or after treatment, thus for example facilitating comparison of the target area before and after treatment, either visually or by image processing. The image of the target area may be an image of any of the tissue parameters mentioned above, such as colour, temperature, etc, or it may be an image of a mathematical function of any of such parameters.

Further, light sources emitting light of different predetermined wavelengths may be directed towards the target area. For example, the light sources may comprise two light emitting diodes, one for emission of light in the wavelength range where the light is considered red and the other for emission of light in the wavelength range where the light is considered green. Also, the light sources may comprise three, four or even more light emitting diodes for emission of light of different wavelength ranges. The light sources may alternatively emit light in the ultra violet or infrared wavelength range. Light from the light sources is transmitted towards the target area and is reflected by tissue at the target area. The reflected light is detected by the detector means and the intensity of reflected light in the two or more wavelength ranges in question characterises one or more parameters of tissue that is illuminated. According to the wavelength selected, different parts of the tissue may reflect the light. Illumination of a tissue target area with a light source emitting light in the wavelength range considered orange may e.g. improve visualization of blood vessels and vascular disorders, while illumination with bluish light will conceal the same structures and improve visualization of less vasculated regions.

The image of the target area may be adapted to control the treatment just completed, or the images may be stored to provide documentation of the treatment, e.g. for clinical a research purposes. Furthermore, one or more images may be stored for documentation of tissue conditions of the target area. The handpiece may, thus, be used for diagnosis purposes. The images may be stored in a memory of the handpiece and the memory may be adapted to be read-out after treatment or diagnosis of the target area.

Alternatively to positioning the sensor on the selector device, the sensor may be positioned behind the deflecting means. Hereby, the sensor may be used during treatment, i.e. while treatment is in progress, so that a feedback during treatment is facilitated. The deflecting means behind which the sensor is positioned may then be provided with special coatings so as to allow for at least partial transmission of light reflected from the target area to the sensor.

For example, when two light sources are utilised for detection of tissue parameters, predetermined reflected light intensity value ranges for the two wavelength ranges may be stored in a memory of the handpiece. During treatment, measured values of reflected light intensity are compared with the stored predetermined ranges and when measured values are within the stored ranges, treatment is enabled and otherwise it is disabled.

The information from the sensor may be displayed on a monitor or a display, such as a CRT, a VFD, an OLED, an LCD, a TFT display, etc. The display may be positioned on the handpiece or it may be an external display coupled to the handpiece. The external display may be connected to the handpiece via a wireless connection, such as a blue tooth connection.

The displayed information may comprise a map of tissue parameters. Furthermore, the handpiece may comprise image-processing means for processing the map for enhancement of selected tissue conditions.

Tissue conditions may be displayed as graphical three-dimensional plots showing surface profiles of selected mathematical functions of tissue parameters of the mapped area. Alternatively, tissue features or tissue conditions may be displayed as a colour map, i.e. predetermined ranges of values of a selected mathematical function of tissue parameters are allocated selected colours to be displayed in areas of the map mapping tissue areas with the respective function values.

The specific tissue conditions or tissue types may hereafter be treated differently e.g. by controlling parameters of the first light beam in response to the detected tissue parameters and/or tissue conditions.

Furthermore, user interface means for user selection of specific mapped tissue areas for treatment may be provided. Hereby, only specific areas containing e.g. warts or moles may be treated without treating areas containing no marks or areas containing e.g. freckles. The specific mapped tissue areas may be of different sizes and shapes, i.e. a specific mapped tissue area may have a shape, which substantially corresponds to the circumference of a corresponding wart or mole on the tissue.

The display may comprise a touch screen for displaying the tissue map and an operator of the handpiece may select a tissue area for treatment by touching the corresponding area on the touch screen.

Alternatively, the user interface means may conventionally comprise a mouse or a track ball for moving a pointer on the display unit for pinpointing tissue areas to be treated.

The user interface means may further provide for selection from a number of predetermined patterns, setting of parameters, etc. The selection and setting of patterns and parameters may be performed by buttons, jog dials, etc. Furthermore, the buttons may be configurable soft-buttons allowing for future software upgrades so that for example implementation of new applications may be performed without any hardware changes.

At least one of the at least two components may be a sensor for measuring the power of the first light beam. Hereby, the measured power and/or fluence may be displayed on the display.

The sensor for measuring the power of the first light beam may be any power sensor, such as a silicon power sensor, a thermopile, a thermal volumetric power sensor, etc.

In some applications, it is of importance that the real value of the output power is known in order to obtain a consistent and uniform treatment, e.g. throughout the day or throughout the month, independently of the age and condition of the apparatuses and light sources used. By measuring the actual power of the first light beam in close proximity of the target area, i.e. after being emitted from the optical fiber, a control signal indicating the measured power may be provided to the light source so that parameters of the first light source may be adjusted according to the measured power of the first light source.

Alternatively, manual tuning of parameters of the first light source may be performed by the operator according to the measured power of the first light beam.

At least one of the at least two components may provide a shutter function, so that the first light beam may be turned on and off at the handpiece, without turning on and off the first light source. When, for example, the first light source has slow turn on and turn off times, the shutter may be used to optically and/or mechanically turn the light source on and off. The on/off time for the shutter may be less than 150 ms, such as less than 100 ms, preferably less than 50 ms, such as less than 25 ms. The shutter turn on/off time will, naturally, be dependent on the mechanics of the selector device.

The shutter may be operated on the basis of an output produced by a sensor measuring characteristics of the first light beam. The sensor may for example be a power meter sensor and the shutter may be opened, if the power of the first light beam increases above or decreases below certain predetermined power levels. The measured power of the first light beam may, thus, be compared to a predetermined threshold value, and the shutter may be opened when the power of the first light beam exceeds the predetermined threshold value. The target area may then be treated according to predetermined settings and by means of the second light beam. The shutter is then closed when the target area has been treated according to the predetermined settings.

Furthermore, the shutter may be operated on the basis of an output produced by processing means analysing measured beam parameters, such as wavelength, intensity, dwell time, pulse duration, duty cycle, etc., of the first light beam. The measured beam parameters may be provided by the sensor connected to the processing means. The sensor may for example be a sensor for measuring the power of the first light beam, and the processing means may analyse the measured power, the spot size irradiated by the treating light beam (which spot size may be predetermined), etc., and further operate the shutter according to a corresponding output, the output, in this specific example, controls the shutter so that the time of irradiation of the spot size is controlled to provide a specific fluence on the target area.

The predetermined settings may comprise settings regarding the total duration of the treatment, and/or settings regarding the traversing pattern of the second light beam on the target area, so that the shutter is closed when the second light beam has performed the traversing pattern. Furthermore, the settings may comprise settings regarding the treatment time at each position to be treated.

For safety reasons a continuous comparison of the power of the light source and another predetermined threshold may be performed, so that the shutter may be closed if the power of the light source exceeds the other predetermined threshold.

The user may be alerted when the shutter has been closed. The user may furthermore be alerted if the temperature of the shutter exceeds a predetermined threshold temperature.

The handpiece may further comprise shutter cooling means, such as cooling fins, for cooling the shutter and/or the power sensor. The shutter and/or the sensor for measuring the power of the first light beam may both be exposed to heat corresponding to the power level of the first light source. For medium and high power light sources, some kind of cooling may be needed to cool the sensor and/or the shutter. Cooling fins may, for example, be provided and mounted at the shutter and/or the sensor.

Alternatively, at least one of the at least two components may be a reflecting mirror being adapted to reflect at least a portion of the first light beam. The handpiece may then comprise absorbing means being adapted to absorb at least a substantial part of the light beam being reflected by the at least one reflecting mirror(s). The absorbing means may for example be positioned on an inner surface of the handpiece.

The absorbing means may comprise a heat sink or, alternatively, a stationary heat sink may be mounted on an inner surface of the handpiece or a heat sink may be mounted on the outside of the handpiece being in thermal contact with the absorbing means.

The handpiece may furthermore comprise a detector device for receiving at least a portion of the light beam being reflected by the at least one reflecting mirror(s), thereby gaining information relating to said light beam, and producing a corresponding output.

The detector device may be positioned on an inner surface of the handpiece. The detector device may, for example, be a power meter for measuring the power of the first light beam. Furthermore, other parameters and/or properties of the first light beam may be measured, such as wavelength, intensity, dwell time, pulse length, etc. The handpiece may be operated on the basis of the produced output.

Especially when using high power light beams, it is an advantage to have a reflecting component positioned in the beam path of the first light beam when measuring or shutting off the first light beam, so that the components at the selector device are not excessively heated. Furthermore, when a high power light beam is directed or deflected into detectors, cameras, etc., large demands are made on the detectors in respect of quality, durability, etc. Furthermore, providing a high power light beam to a detector may imply that cooling of the detector may be necessary or desirable, whereby placement of the detector on the selector device may be inconvenient.

Another advantage of using a reflective component on the selector device for selecting one or more of the at least two components on the selector device, is the space requirements of the components which may be easier to comply with when the components are positioned away from the selector device, for example on an inner surface of the handpiece.

At least one of the at least two components may be a non-linear medium, such as a non-linear crystal, such as a $BaTiO_3$, a KTP, a $KNGO_3$, a $LiNGO_3$, a $BaB_2O_2$ (BBO), a periodically poled $LiNGO_3$ (PPLN), a periodically poled KTP (PPKTP) crystal, etc., such as at least a part of an optical parametric oscillator (OPO), such as the non-linear medium of the OPO, such as a KTP, a $KNGO_3$, a $LiNGO_3$, a BBO, a PPLN, a PPKTP crystal, etc. The first light source may then pump the non-linear medium to achieve the non-linear effects provided by the non-linear medium, such as frequency doubling, tuneable wavelength etc.

At least one of the at least two components may be a diaphragm, such as an iris diaphragm. It is hereby possible to leave out or cut off parts of the first light beam.

Furthermore, at least one of the at least two components may be a collimator, such as a collimating lens, for collimating the first light beam. Hereby, a collimating light beam is directed towards the deflecting means, ensuring a uniform deflection of the light beam.

It is envisaged that more optical elements may be combined at the individual components of the selector device. For example, one component of the selector device may comprise a diaphragm and a collimator. Hereby, a more well-defined light beam may be directed towards the deflecting means enhancing the optical properties of the second light beam. Another example may be the combination of a shutter and a sensor, so that one component of the selector device comprises a sensor providing information about the target area, such as properties or parameters of the target area and the tissue at the target area, and a shutter for shutting off the first light beam. The first light source is, thus, not turned off at the light source during sensing, but merely shut off by the shutter. The shutter may, furthermore, be a combination of a reflective mirror mounted at the component along with the sensor, and absorbing means adapted to absorb the reflected beam. In this example, the shutter or the reflective mirror may be provided on the reverse side of the sensor.

Still further, different filters may be inserted in front of one or more of the component(s) such as in front of a camera or a sensor so as to alter the relative intensity of the different wavelength components of the light beam incident on the camera or sensor. The filters may for example be positioned on another selector device, the other selector device being adapted to move independently of the selector device comprising the camera or sensor.

The deflecting moving means may be adapted to cause the second or third light beam, if present, to traverse the target area in a predetermined pattern. The predetermined pattern may e.g. be one or more straight lines, so that the second light beam traverses the target area line by line. Hereby, target areas of any arbitrary shape, such as polygonal, such as rectangular, quadratic, triangular, etc, or circular, elliptic, etc, may be traversed line by line by appropriately controlling the starting point and stopping point of light emission along each line traversed. The lines may be traversed sequentially i.e. neighbouring lines are traversed successively. The lines may be traversed in a meanderlike pattern or, preferably, the lines may be traversed starting from the same side and, still further, it is preferred to use the shutter to prevent emission of the second light beam towards the target area during repositioning of the deflecting means. Alternatively, an interlacing pattern may be used.

A scan pattern employing more than one spot size may be provided. To provide such a scan pattern, at least two of the at least two components may be optical lenses, the lenses having various optical parameters resulting in various spot sizes on the target area, depending on the component selected. A spot size is, thus, selected by selecting a lens providing a spot of the corresponding spot size, and the target area is traversed in a predetermined pattern of spots having the selected spot size.

Subsequently, a second spot size is selected by selecting a lens providing a spot of a corresponding spot size, and the target area is traversed in a second predetermined pattern of spots having the second spot size.

The target area may, thus, be traversed two or more times. The target area may for example be traversed a first time by the second light beam having a first spot size on the target area, followed by a second traversing by the second light beam having a second spot size on the target area. The first spot size may be a relatively large spot size filling the target area with a limited number of treatment spots, whereafter the second traversing wherein the second light beam has a second, relatively small, spot size on the target area so as to fill in the space between the treatment spots of the first size. The speed of the scanning may thus be increased by the use of relatively large spot sizes while the uniformity of the scanning pattern is intact.

For example when removing hairs, the target area may be traversed a first time by the second light beam having a relatively large spot size and a fluence selected to treat unwanted hair growth. The treatment of excessive hair growth may require a number of treatments, e.g. over months, before a visible result is obtained. A second scan having a power density being high enough to carbonize the hair shafts may, thus, ensure a visible result event after the first treatment. The higher power density may be obtained by keeping the laser power setting constant while selecting a smaller spot size.

Furthermore, a first scan may be performed for collection of information regarding the target area, such as information about tissue conditions, etc., followed by a second scan for treatment of the target area in response to the collected information. The target area may for example be illuminated by a second light source, such as a white light source, and the reflected light from the target area may be detected by the detector and analysed so as to characterise the tissue that is illuminated. The following treatment scan may then treat the entire target area or selected part(s) of the target area, and control parameters of the second or treating light beam according to the information collected. The second light source may be a light source illuminating substantially the entire target area or the second light source may illuminate one spot on the target area and be adapted to traverse the target area while information of the reflected light is provided to the detector. Having a second light source illuminating substantially the entire target area, collection of information may either be taken by a camera, such as a CCD camera, collecting information of substantially the entire target area at the same time, or the information may be collected from one spot at a time, deflecting reflected light from the target area onto the detector during scanning of the target area.

It is envisaged that a first scan providing information about the target area does not necessarily need to be followed by a treatment scan. The handpiece according to the invention may, thus, be used for diagnosis of the target area. The information provided by the handpiece may then be stored and/or read out to provide basis for another treatment or provide basis for a decision of which kind of treatment of the target area to initiate.

The handpiece may, still further, comprise tissue cooling means for cooling the tissue of the target area. Depending on the power dissipation in the tissue, the wavelength used, etc., the tissue will be heated during treatment. In order to minimise damage to the tissue not to be treated, a tissue cooling means may be provided to reduce the temperature of the tissue before, during and after treatment.

The handpiece may further comprise at least one second light source for providing illumination of the target area. By illuminating the target area sensing of, e.g. tissue parameters, is more easily facilitated. Furthermore, it is an advantage to illuminate the target area so as to increase the visibility of the target area for the user.

The at least one second light source(s) may be one of the at least two components. Hereby, different light sources may be used, for example, for illumination of the target area before and after treatment. The second light source may also be used during sensing while sensing with an optical detector when the optical detector is not positioned at the selector device. Alternatively, one of the at least one components at the selector device may comprise the second light source as well as an optical detector.

Furthermore, the handpiece may comprise a distance piece for defining the distance between the output of the handpiece and the target area, and at least one of the at least one second light source(s) may be mounted on said distance piece. Hereby, larger second light sources may be used. Furthermore, higher power second light sources may be used if the airflow is sufficient and if adequate heatsinks are provided. However, the positioning of the light source may imply that the light is illuminating the target area under an angle, whereby shade effects may occur.

Still further, at least one of the at least one second light source(s) may be mounted at or near the output of the handpiece. The at least one-second light source may, thus, be mounted at or near the deflecting means, such as at or near an output lens of the handpiece. For example, a row of light emitting diodes (LED's) or incandescent lamps may be provided around the output lens. Furthermore, different types of light sources may be provided at the same time thereby providing a choice of illumination wavelengths. By positioning the at least one second light source around the output lens of the handpiece an illumination of the target area having substantially no shade effects is obtained.

At least a substantial part of the light output of at least one of the at least one second light source(s) may have a wavelength in the infrared part of the electromagnetic spectrum, such as in a wavelength range from 0.75 µm to 100 µm, such as in a near infrared part of the spectrum, such as from 0.75 µm to 1.5 µm, such as in a middle infrared part of the spectrum, such as from 1.5 µm to 30 µm, such as in a far infrared part of the spectrum, such as from 30 µm to 100 µm. Alternatively or concurrently, at least a substantial part of the light output from at least one of the at least one second light source(s) may have a wavelength in the visible part of the electromagnetic spectrum, such as in a wavelength range from 0.390 µm to 0.770 µm, and alternatively or concurrently, at least a substantial part of the light output from at least one of the at least one second light source(s) may have a wavelength in the ultraviolet part of the electromagnetic spectrum, such as from 10 nm to 390 nm, such as in the near ultraviolet part of the spectrum, such as from 300 nm to 390 nm, such as in the far ultraviolet part of the spectrum, such as from 200 nm to 300 nm, such as in the extreme ultraviolet part of the spectrum such as from 10 nm to 200 nm.

There may, thus, be provided a plurality of second light sources, each light source emitting, at least partly, light in the ultraviolet, visible, and/or infrared part of the electromagnetic spectrum. The light from the plurality of second light sources may then be combined to suit the desired application.

The second light source(s) may be any light sources capable of illuminating the target area, such as LED's, such as high brightness LED's, full colour LED's, infrared (IR) LED's, or ultraviolet (UV) LED's, such as laser diodes, krypton lamps, such as small lens-end krypton lamps, such as infrared (IR) lamps, incandescent lamps, such as small lens-end regular incandescent lamps, etc. For example, for illumination during sensing, high power low lifetime light sources, such as incandescent light sources, krypton light sources, such as halogen lamps and bulbs, etc., may be used by ensuring that the light sources are only turned on during sensing. Generally, LED's have longer lifetime (100000 hours) and higher efficiency while incandescent and krypton light sources have higher output and lifetime in the range of 1000-100000 hours.

The handpiece may still further comprise means for displaying an image on the target area. The image may be displayed by means of light, at least a substantial part of which has a wavelength in the visible part of the electromagnetic spectrum. The means for displaying an image on the target area may comprise a light source such as one or more light emitting diode(s) (LED's), and/or one or more laser diode(s). Furthermore, the image may be displayed by means of light having various wavelengths and/or by means of light having various intensities.

When the deflecting means is adapted to cause the treating light beam to traverse the target area in a predetermined pattern, the image displayed on the target area may for example outline the area(s) of the target area that will be treated if a corresponding pattern is selected.

The scan pattern within each area may further be displayed on the tissue, so that the predetermined patterns, including any fade-in and fade-out effects, are shown on the tissue. The image may be displayed using full colour LED's or laser diodes.

Information of the target area may be collected by a sensor and provided to image processing means, such as a processor, for generating an optimal pattern in which to treat the target area. An image of the generated pattern may be shown directly on the tissue. The user may accept the generated pattern and choose to treat the target area according to the generated pattern or the user may modify the generated pattern, so that for example, specific areas are not treated, etc.

Furthermore, the user may be able to modify the chosen parameters of the first light source before treatment is initiated.

The handpiece may, furthermore, comprise a display, such as a graphical display, so that an image of the generated pattern may be shown on the display in addition to or alternatively to providing the image at the target area. The display may also show information regarding the optimal parameters of the first light beam. The user may then provide changes to the generated pattern as well as to the generated optimal parameters of the first light source, etc. before the treatment scan is initiated.

The display may, for example, be mounted on an upper surface of the handpiece. Hereby, the user may be able to see the display irrespective of which hand is used. The image may be adapted to be rotated digitally, so that a rotation of 180 degrees when the hand is changed ensures that the image and any text on the display will turn upside down. Furthermore, soft buttons may be digitally (re)configured to the hand used by the operator. Alternatively, the display may be able to display information in a user specified direction by mechanical means, so that the display may be hinged or rotatably mounted in any other way so that the user may decide the position of the display, e.g. according to which hand is used to hold the handpiece.

The handpiece may, still further, comprise a built-in light source for producing a treating light beam to be deflected onto the target area. The treatment light beam produced by the built-in light source may be a highly focused light beam, such as a beam emitted from a laser diode, and may be adapted to form a spot on the target area, said spot having a high fluence and a small spot size. The power density may for example be in the range of 5-50 kW/cm$^2$, such as 10-30 kW/cm$^2$, such as preferably 20-25 kW/cm$^2$, and furthermore a spot size smaller than ⅕ mm, such as ¹⁄₁₀ mm may be provided by the built-in light source.

It is an advantage of the built-in light source that the light beam emitted from the built-in light source does not have to be led through an optical fiber from the light source to the handpiece. It is an advantage that the emitted light beam is not subjected to losses due to e.g. dispersion in the optical fiber, coupling losses in both ends of the optical fiber, absorption and attenuation in the optical fiber, etc. Hereby, the quality of the light beam emitted from the built-in light source may be maintained, so that a highly focused light beam may be deflected towards the target area.

The built-in light source may comprise a laser device, such as a laser diode, a LED, such as a high-power LED, a flash lamp, etc. or the light source may comprise any array(s) or matrix(ces) of such light sources, such as array(s) of laser diodes, array(s) of LED's, etc.

The built-in light source may be the first light source, so that no external light source has to be provided to the handpiece. Alternatively, the built-in light source may be an additional light source so that two light sources may be provided. Hereby different properties of the two light sources may be used to optimise the treatment. The first light beam emitted from the first light source may, for example, have a first wavelength and the treating light beam emitted from the built-in light source may have a second wavelength, and the first wavelength may be different from the second wavelength. Alternatively, the first and second wavelength may be substantially identical, so that the different optical properties of the two light beams are utilised or so as to provide a second or treating light beam having a higher power.

Treating of tissue with two or more wavelengths may provide effects not obtainable by the use of a single wavelength light source. For example, when performing selective photothermolysis, the absorption of infrared light in the blood may be enhanced by concurrently use of pulsed green light. The pulsed green light causes photochemical and photothermal modifications to the chemical constituents of blood which results in enhanced infrared absorption in the thus modified blood. The end-result is then better than possible when using a single wavelength only (Cooperative Phenomena, 'Two-pulse, Two-color Laser Photocoagulation of Cutaneous Blood Vessels', John F. Black et al., Division of Biomedical Engineering, The University of Arizona). Another example may be found in U.S. Pat. No. 6,358,243 describing a dual wavelength application during dermal ablation. A light beam at 6.45 micron is absorbed by proteins in tissue so that the mechanical structures of the tissue are softened, while a light beam at 3.01 micron absorbed by water in the tissue causes the softened tissue to dislodge. By such a two-wavelength application a lower degree of collateral damage is obtained.

Furthermore, the two or more wavelengths may be provided by a single light source being able to be tuned to the two or more wavelengths. Alternatively, two or more light beams being emitted from two or more respective light sources may be coupled into the handpiece or the two light beams may be coupled into a single optical fiber to be coupled into the handpiece.

The handpiece may further comprise at least one external connection, said external connection(s) preferably being connected to the handpiece in a direction being at least substantially parallel to a longitudinal axis of a handle of the handpiece, thus making the external connection of the least possible inconvenience to the user.

The at least one external connection may comprise connection to the first light source, electrical connections, such as power connection, connection to an external display, etc.

The handpiece may furthermore comprise an attachment part for removably attaching one or more device(s) to the handpiece. The attachment part may comprise a magnet or a mechanical gripper so as to removably attach the one or more devices.

It is, however, envisaged that the attachment parts may just as well form part of the handpiece and the removable attachment is optional for providing a flexible handpiece. Furthermore, a combination of attachment parts and parts forming part of the handpiece may be used. The handpiece may for example comprise a cooling system providing a cooling fluid to an attachable tissue cooling means, such as a cooling member for cooling tissue of the target area.

At least one of the one or more device(s) may be a distance piece for defining the distance between an output of the handpiece and the target area. In this way, the operator of the handpiece is assisted in keeping a constant distance from the output of the handpiece to the target area. Hereby, it may be ensured that the second light beam and/or the treating light beam will be focused on the target area during a treatment cycle.

Another of the one or more device(s) may be a tissue cooling means for cooling the tissue of the target area. By removably attaching the tissue cooling means to the handpiece, the tissue cooling means may be an option only provided to treatments requiring cooling of the tissue of the target area. The attachment part may comprise means for providing a cooling fluid, such as a gel, water, etc. to the tissue cooling means. The tissue cooling means may be provided with an outlet or a nozzle for applying a cryogenic fluid to the target area before, during or after the treatment. The cryogenic fluid may be 1,1,1,2-tetrafluoroethane, etc.

The means for providing a cooling fluid may form an entire cooling system or the means may form a connection part to a cooling system at least partly forming part of the handpiece.

The fluid may, for example, be applied between two plates of a material transparent to the light beams to be used during sensing and/or treatment. The fluid may be provided in a substantially closed reservoir between the two plates or the reservoir may be provided with an in-let and an out-let whereby the fluid may pass through the reservoir to ensure constant cooling during treatment.

Alternatively, the tissue cooling means may comprise a disc or a plate of a material transparent to the light beams to be used during sensing and/or treatment. The cooling fluid may then be guided at least partly around the disc or plate, or around a closed reservoir comprising a cooling fluid or another fluid, so as to cool the tissue cooling means. The guide around the disc or plate may be a closed guide comprising a cooling fluid, or the guide may be provided with an in-let and an out-let whereby the cooling fluid may pass through the guide to ensure a constant cooling during treatment. It is an advantage that the cooling fluid, at least partly, encircles the disc or plate so that the cooling fluid does not need to be transparent to the light beams used during sensing and/or treatment.

In the case an in-let and an out-let of the reservoir or guide is provided, the cooling fluid may, preferably on the out-let side of the reservoir or guide, beled through the handplece for cooling elements of the handpiece. The cooling fluid may, thus, on returning from the tissue target area, cool the deflecting mirrors, the shutter, the absorbing means, etc. or the cooling fluid may be used to generally cool the handpiece.

The handpiece may still further comprise a sensor for measuring the temperature of the target area. The sensor may be positioned on the tissue cooling means. The temperature sensor may be a contact sensor for measuring the temperature of the tissue touching the sensor or alternatively, the sensor may be an infrared detector, such as an infrared photo detector, for detection of intensity of infrared light emitted from tissue at the target surface, e.g. for determination of the temperature of the tissue.

One of the one or more devices to be removably attached to the handpiece may be a second light source for illuminating the target area.

Furthermore, the handpiece may comprise means for supplying power to at least one of the one or more devices.

BRIEF DESCRIPTION OF THE DRAWINGS

FIGS. 5A and 5B show two different scanning patterns, FIG. 6 shows three different possible positions for a light source.

DETAILED DESCRIPTION OF THE DRAWINGS

Figure 1:
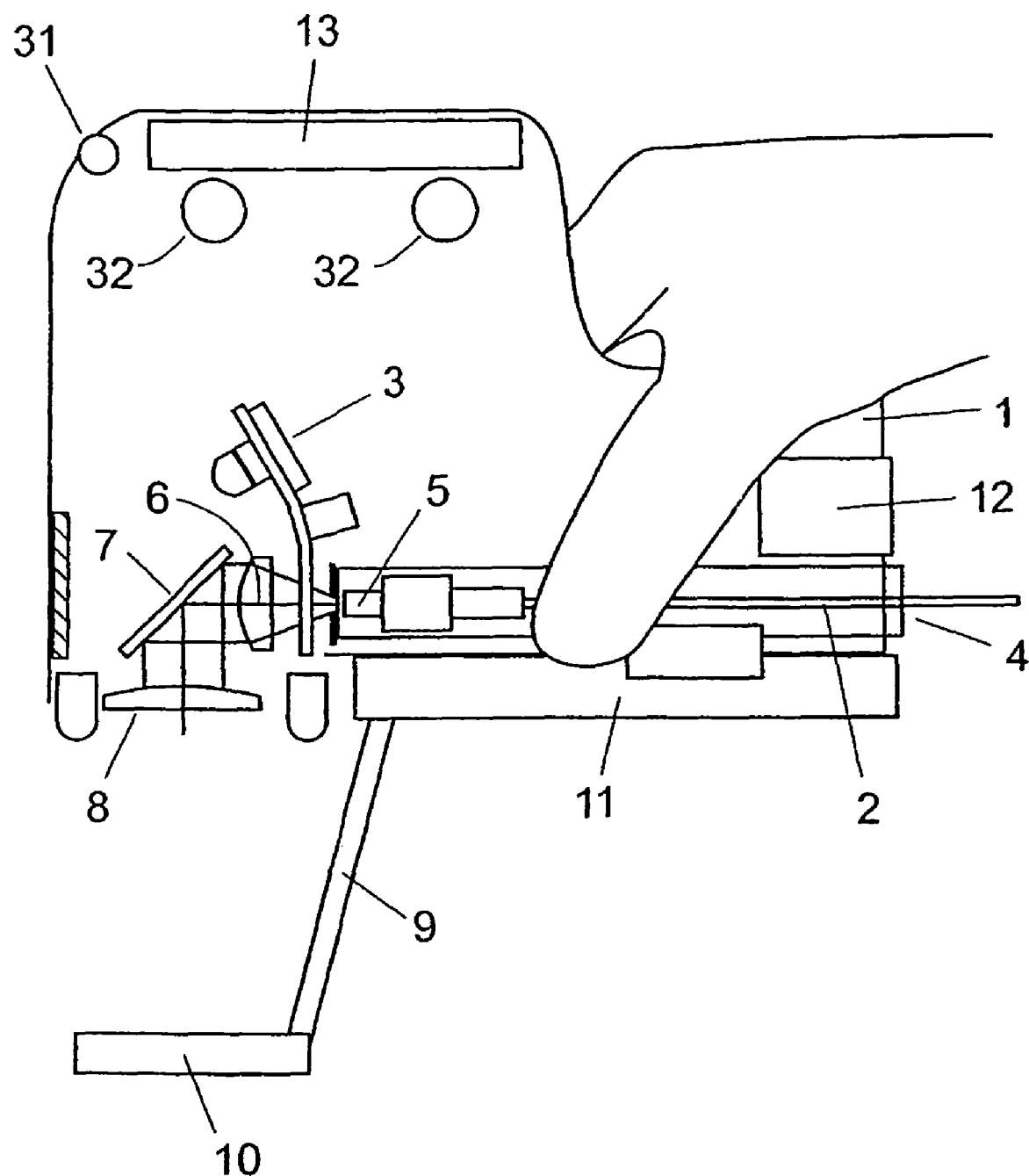
FIG. 1 shows a side view of a handpiece as well as an overview of the contents of a handpiece according to the present invention.

FIG. 1 shows a side view of a handpiece according to the present invention. The handpiece comprises a handle 1, an optical fiber 2, and a circular selector device 3. The optical fiber has receiving means comprising an input end 4 being adapted to be connected to an external light source (not shown), and an output end 5 from where the light beam is emitted into the handpiece. When the light beam is emitted from the output end 5 of the optical fiber 2, it passes through a selected component 6 of the circular selector device 3. In this case the selected component 6 is a lens. The light beam is then deflected onto a target area via deflecting means comprising deflecting mirror 7 and output lens 8.

The handpiece is further provided with a distance piece 9 and a cooling member 10 for cooling the tissue at the target area. The distance piece 9 and the cooling member 10 in combination ensures that a certain desired distance is kept between the output lens 8, i.e. the position in which the treating light beam exits the handpiece, and the target area. This ensures a homogeneous treatment of the tissue. The distance piece 9 shown in FIG. 1 furthermore functions to convey cooling fluid to and from the cooling member 10. The cooling fluid is supplied via cooling supply 11.

The handpiece also comprises an electrical supply 12 for supplying power to the handpiece. A display 13 is mounted on an upper part of the handpiece. The display is adapted to show fluence, power, dwell time, outline of the scanned target area, an image of the target area to be treated, etc. A lasing indicator 31 is positioned on the handpiece for indication of laser operation. Furthermore, user interface means 32 are mounted on the handpiece. The user interface means may be buttons, switches or a jog dial for setting of parameters.

Figure 2:
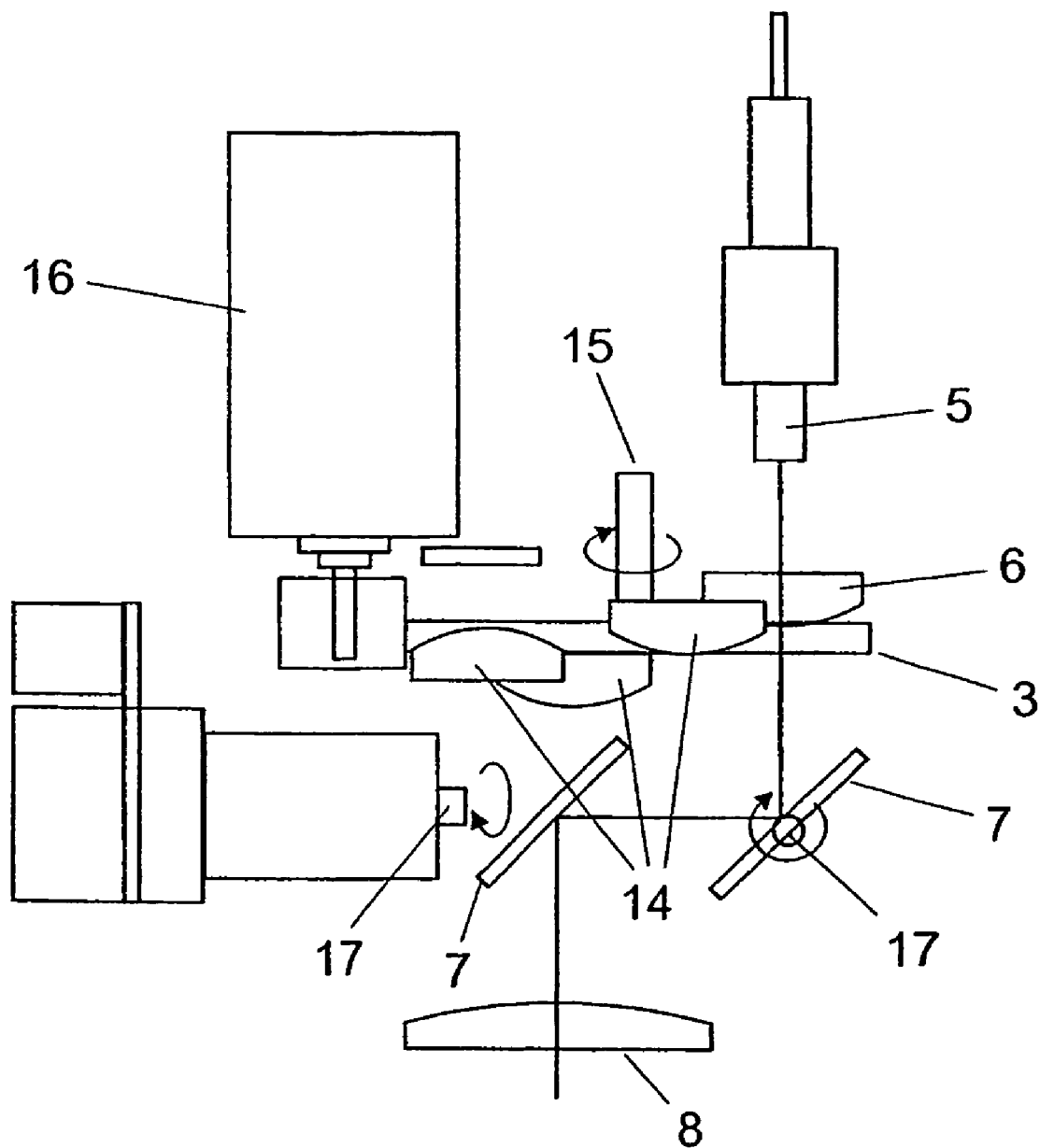
FIG. 2 shows the beam path through a handpiece according to the present invention having a circular selector device.

FIG. 2 shows the beam path through a handpiece according to the present invention. The handpiece has a circular selector device 3 having a number of different components 6, 14 mounted thereon. The circular selector device 3 is rotatably movable about a symmetry axis 15 of the device 3, so that the selected component 6 may be replaced by one of the other components 14 by simply rotating the circular selector device 3 until the desired component 14 is positioned in the beam path. The components 6, 14 may, e.g., include various lenses, a shutter, one or more sensors for providing information regarding the tissue of the target area, a light source, a laser power meter, etc. Thus, a component 6, 14 can be chosen according to the needs and desires of the current situation or application. Thus, in case a shutter function is needed, a shutter component is chosen, in case a specific spot size on the target area is needed or desired, a lens having optical properties producing the needed/desired spot size is chosen, etc. The moving means for moving the selector device, i.e. rotating the circular selector device 3, comprises a motor 16.

The selector device 3 is rotatably movable about the symmetry axis 15 and the means for moving 16 is a geared motor and an encoder adapted to provide a high degree of repeatability. This mechanical construction is simple and reliable. The motor is a 1516SR Faulhaber motor with a 22:1 zero backlash spur gearing and a magnetic 512 position encoder, e.g. an IE2-512, so that there is no risk of optical disturbances by any of the light sources. This combination provides a fast positioning time in the range of 100-200 ms for half a turn and a positioning resolution of 0.0016 deg, which is 3.3 μm with a 12 mm circumference of the disc (corresponding to 22528 encoder pulses per round). The pre-tensioned zero backlash gearing allows for a low noise operation and an accurate steady state positioning without introducing the backlash of normal spur gears, usually 2-4 deg. The motor construction consumes no power in a fixed position and only little power while moving and are furthermore rated for 10000 hours of continues operation. The electrical communication with the disc components may be a flexible PCB, such as a PFC. A plug (not shown) may be provided to facilitate exchange of selector devices.

The handpiece of FIG. 2 comprises two deflecting mirrors 7 being pivotally movable about respective pivot axes 17 being substantially perpendicular to each other and to the symmetry axis 15 of the circular selector device 3. The two deflecting mirrors 7 may be adjusted so as to position the spot of the treating light beam in a desired position on the target area. They may further be adapted to cause the treating light beam to traverse the target area in a predetermined pattern.

Due to the selector device 3 the process of replacing one component 6 by another component 14 is very easily performed. All the components 6, 14 are positioned inside the handpiece, and it is therefore not required to disassemble the handpiece in order to replace the selected component 6. The process is so easily performed that it is possible to replace a component 6 during the treatment of a patient. This may, e.g., be desirable in case the user needs to gather information regarding the tissue at the target area before choosing the correct scanning pattern, spot size, fluence, etc. In this case the user may first select a sensor device and subsequently a lens having appropriate optical parameters. It may further be desirable to use two or more different lenses during a treatment, e.g. in order to ensure a homogeneous treatment of the tissue. This will be further described below.

Figure 3:
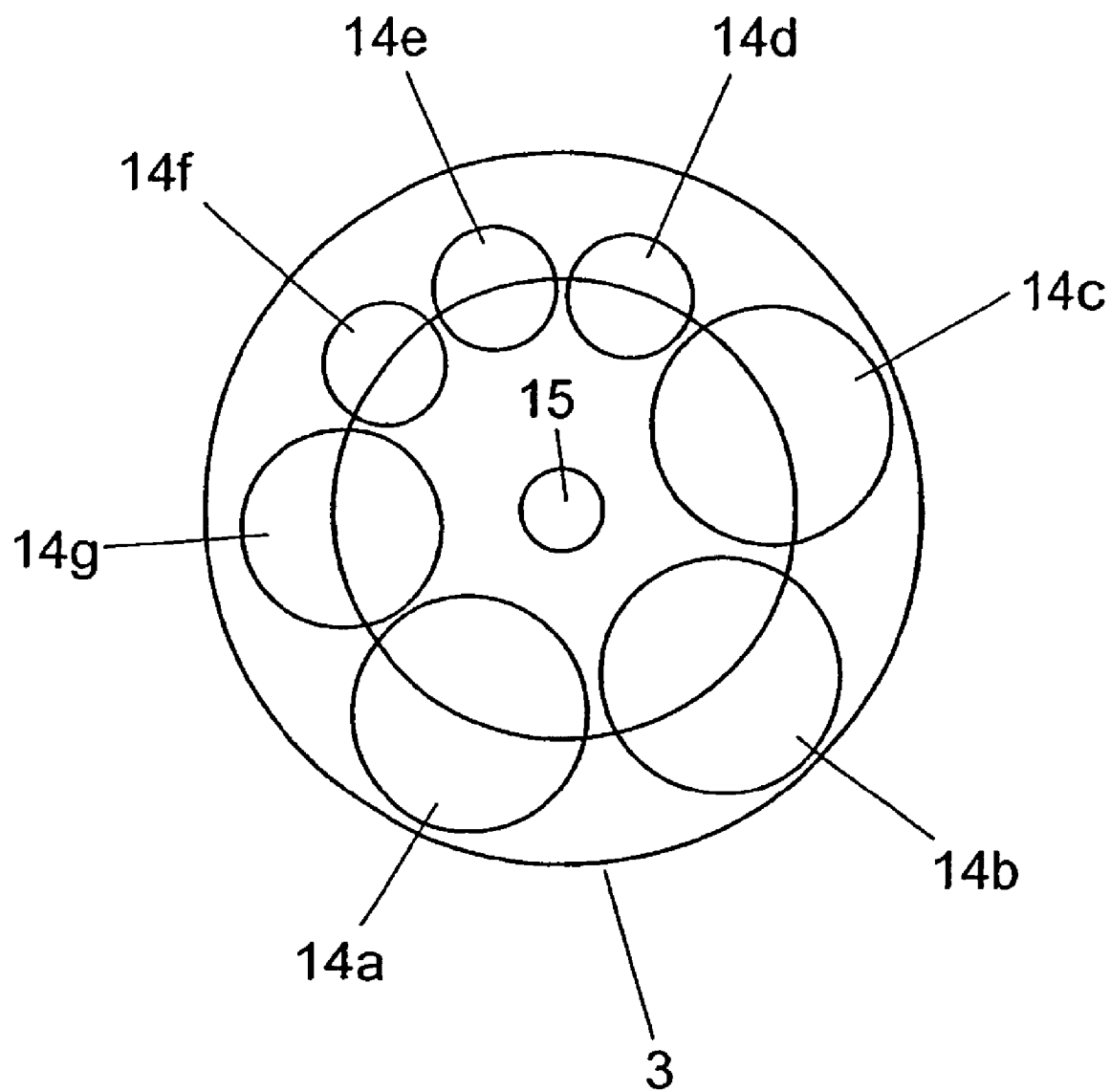
FIG. 3 shows a circular selector device having seven different components.

FIG. 3 shows a front view of a circular selector device 3 having seven different components 14 arranged annularly along the outer edge of the circular selector device 3. In this case three lenses 14a, 14b, 14c, two sensors 14d, 14e, and a guide beam LED or laser 14f are present. Furthermore, one position 14g may be used for an image array, a shutter or a laser power meter.

Figure 4:
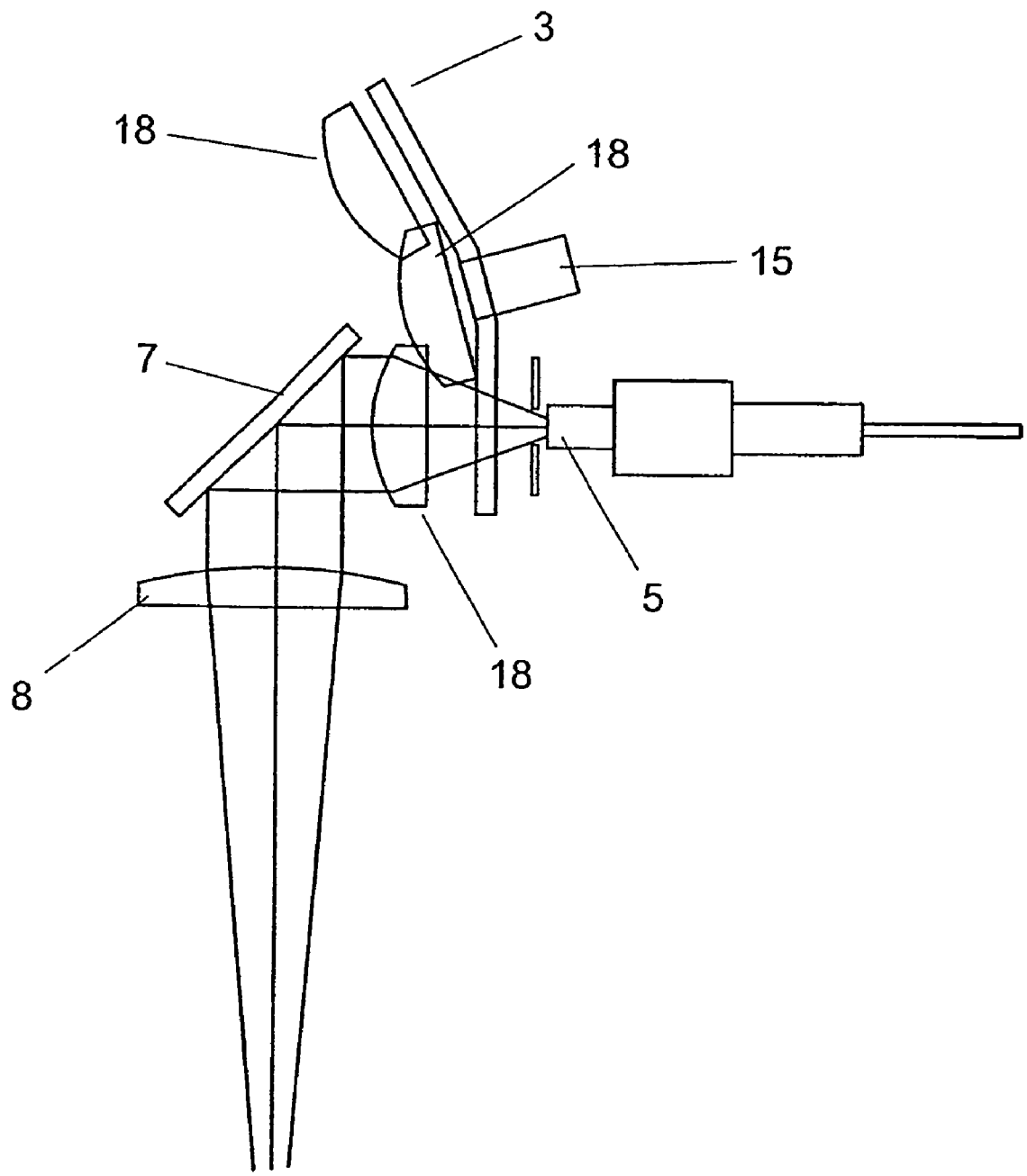
FIG. 4 is a front view of a circular selector device having a number of different lenses, and being positioned in a handpiece.

FIG. 4 is a front view of a circular selector device 3 having a number of different lenses 18, and being positioned in a handpiece. By rotating the circular selector device 3 about the symmetry axis 15, any of the lenses 18 may be positioned in the beam path, thereby choosing a corresponding spot size. Thus, a number of different spot sizes may easily be chosen as described above without changing the output lens 8 or the distance between the output lens 8 and the target area.

FIGS. 5A and 5B show two different scanning patterns using two different spot sizes. The scanning pattern in FIG. 5A comprises nine large spots 19 positioned adjacently without an overlap between the spots 19. The scanning pattern further comprises four smaller spots 20 positioned between the larger spots 19 so as to fill out the gaps introduced because of the circular shape of the larger spots 19. The diameter of the smaller spots 20 is chosen in such a way that as much of the gaps as possible is filled out by the smaller spots 20 without introducing an overlap between the spots 19, 20. Thereby a very homogeneous treatment is obtained, i.e. a minimal total area receives no treatment, and a minimal total area receives double treatment (due to an overlap). Preferably, the pattern shown in FIG. 5A is obtained by selecting a lens providing the large spots 19 and traversing the target area while this lens is positioned in the beam path. The target area is traversed according to the pattern shown in FIG. 5A. Subsequently, a lens providing the smaller spot size 20 is selected and the target area is traversed with this lens positioned in the beam path and according to the pattern shown.

The scanning pattern shown in FIG. 5B comprises four large spots 19 positioned adjacently with a small overlap between the spots 19. Twenty smaller spots 20 surround the four large spots 19. Thus, the edge of the scanning pattern is much more straight than would be the case if only large spots 19 had been used. On the other hand, the total time required for performing a scan is greatly reduced by letting the 'interior' part of the scanning pattern be made by larger spots 19 in stead of choosing the smaller spots 20 for the entire scanning pattern. Furthermore, the risk of introducing errors (e.g. unintentional overlaps or gaps between spots 19, 20, etc.) is greatly increased as the total number of spots 19, 20 making up the scanning pattern increases. It is therefore a great advantage that various spot sizes may be selected, even within the same treatment session.

The scanning patterns shown in FIGS. 5A and 5B illustrate that the handpiece according to the present invention provides the possibility of easily producing a large variety of scanning patterns, i.e. it is possible to design the scanning pattern to suit the situation, e.g. based on type of treatment, skin type, size or shape of treatment area, etc. The same scanner may therefore be used for a number of different purposes, thereby providing a very flexible device. This is a great advantage of the present invention.

FIG. 6 shows three different possible positions for a light source 21. The light source 21a may be positioned on the circular selector device 3, i.e. it may be one of the components of the selector device 3. Hereby, different light sources may be used, for example, for illumination of the target area before and after treatment. Alternatively, one or more light sources 21b may be positioned adjacent to the output lens 8. By positioning the light sources 21b around the output lens of the handpiece, an illumination of the target area having substantially no shade effects is obtained. Finally, a light source 21c may be positioned on the distance piece 9, so as to facilitate the use of larger and higher power light sources 21c may be used.

Figure 7:
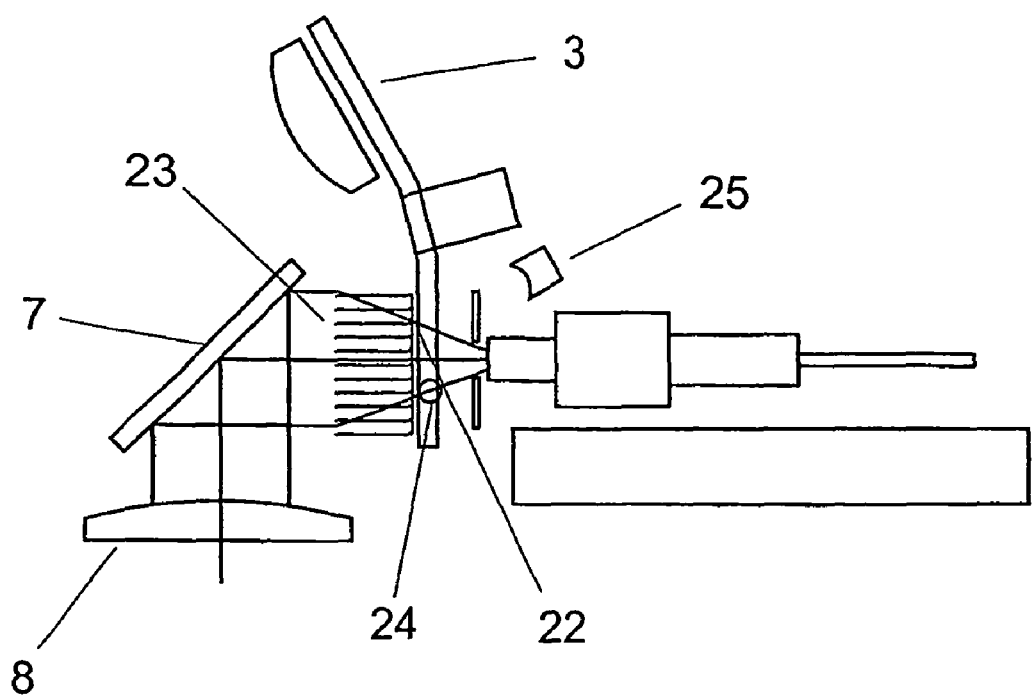
FIG. 7 shows a circular selector device with a shutter, and being positioned in a handpiece.

FIG. 7 shows a circular selector device 3 with a shutter 22, and being positioned in a handpiece. The shutter 22 is positioned in the beam path. Therefore, when the shutter 22 is closed, heat originating from the light beam is dissipated in the shutter. In order to prevent the shutter 22 from overheating it is provided shutter cooling means, such as cooling fins 23. Furthermore, a temperature sensor 24 is positioned at the shutter 22 in order to monitor the temperature of the shutter 22. In case the temperature exceeds a level beyond which there is a risk of damaging the shutter 22, or even the handpiece itself, an alerting signal, e.g. an audible or a visible signal, may be sent to the user. The user may then react to the signal, e.g. by turning off the laser or opening the shutter 22. In case the user does not react to an alerting signal and the temperature of the shutter 22 consequently continues to increase, the handpiece may automatically turn off the laser in order to prevent damage.

The shutter 22 may, e.g., be used when a laser having relatively slow turn on/turn off times is used. In this case the shutter 22 may be kept closed while the laser turns on. When the laser reaches the desired power level, the shutter 22 may be opened and the treatment is performed. When the treatment has been completed, the shutter 22 may be closed again while the laser is turned off. Thus, the tissue at the target area is treated with light beam having a substantially constant power level, thereby providing a very homogenous treatment, even if the laser is relatively slow. Furthermore, the shutter 22 may be closed while the beam is moved between scanning lines. This is particularly useful when the light source is a continuous wave laser.

The handpiece of FIG. 7 is further provided with a detector device 25, such as beam pickup sensor 25, positioned behind the circular selector device 3. At least a small portion of the beam is reflected onto the beam pickup sensor 25 in order to measure the characteristics of the beam. Such a measurement may be used when operating the handpiece. Thus, the scanning pattern may be selected on the basis of a measurement, or the shutter may be operated using the measurement, e.g. in case it is measured whether or not the laser has reached a desired power level, etc.

Figure 8:
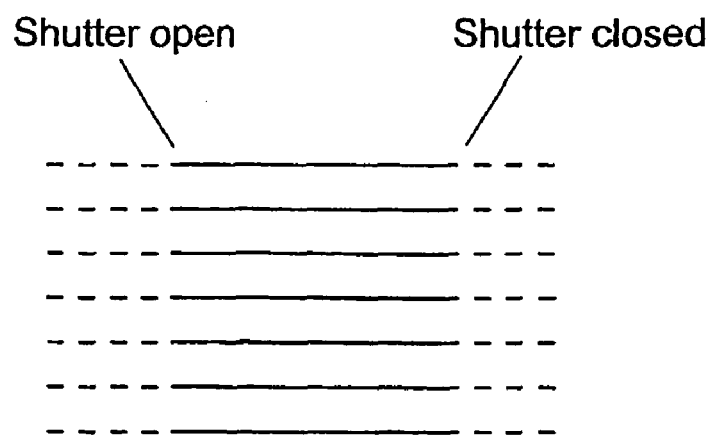
FIG. 8 shows a line scanning application.

FIG. 8 shows a line scanning pattern produced by an apparatus according to the present invention, the apparatus comprising a shutter. Going from left to right in the figure, the pattern is produced in the following way. Initially, the shutter is closed while the laser is turned on. When the laser has reached a desired level with respect to, e.g., power, the shutter is opened and the treatment is performed. When a line has been scanned, the shutter is closed again while the laser is turned off and/or moved to the position where the next line is to be scanned. This is a great advantage when the laser used is slow with respect to turn-on/turn-off and/or with respect to movement of the laser spot. Using the shutter it is possible to obtain a 'clean' line scan, i.e. a line scan wherein the power delivered by the laser to the tissue is uniform, even with a relatively slow laser or laser system.

Figure 9:
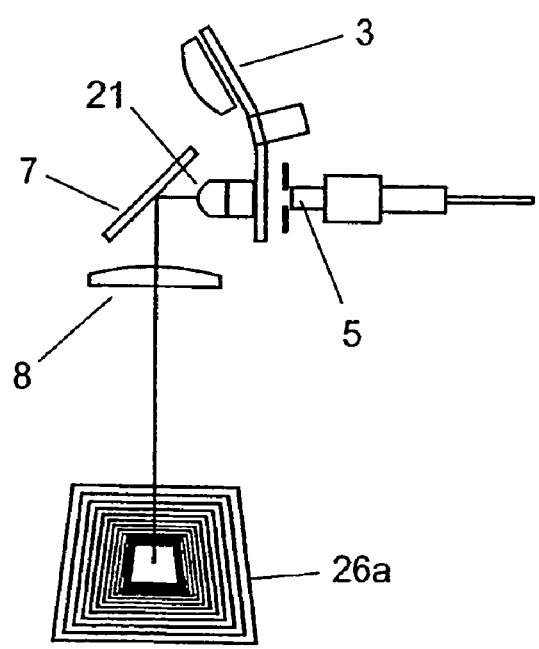
FIG. 9 shows an image projection on the target area caused boa full colour LED.

FIG. 9 shows an image projection 26a on the target area caused by a full colour LED 21 mounted on the circular selector device 3 and positioned in the beam path by rotating the circular selector device 3 to the appropriate position. The image projection 26a produced in this manner is typically a full colour, low resolution image. Such a full colour image projection 26a could, e.g., be used to display a treatment pattern on the target area, various colours illustrating, e.g., various treatment times, power levels, etc. Alternatively or additionally, the image may illustrate fading effects, various colours in this case preferably corresponding to various power levels of the applied laser light.

Figure 10:
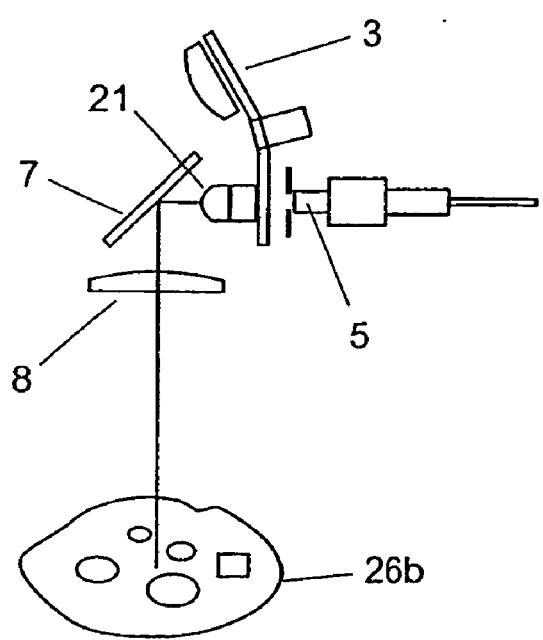
FIG. 10 shows an image projection on the target area caused by a laser diode.

FIG. 10 shows an image projection 26b on the target area caused by a laser diode 21. This is very similar to the situation described above. However, a laser diode is very suitable for displaying a suggested treatment pattern directly on the target area, e.g. in case only specific sub-areas of the target area shall be treated. This may, e.g., be the case if the target area contains a number of warts (needing treatment) and a number of moles (which should not be treated). In this case it should be ensured that only the warts are treated, and this is very easily seen if the suggested treatment pattern is displayed directly on the target area. If, erroneously, one or more of the moles is/are marked as an area needing treatment and/or one or more of the warts is/are not marked, this could be corrected before the actual treatment is performed, thereby ensuring a correct treatment of the patient. The fact that the suggested treatment pattern is displayed directly on the skin instead of, e.g., on an external screen, provides a very illustrative display, where the suggested treatment is shown where the actual treatment will eventually take place. The user may therefore readily and easily determine whether or not the suggested treatment is in fact the desired treatment and optionally request needed alterations to the suggested treatment before the actual treatment is performed.

Furthermore, the light sources 21 described above (i.e. the full colour LED of FIG. 9 and the laser diode of FIG. 10) may be used for illuminating the target area.

Figure 11:
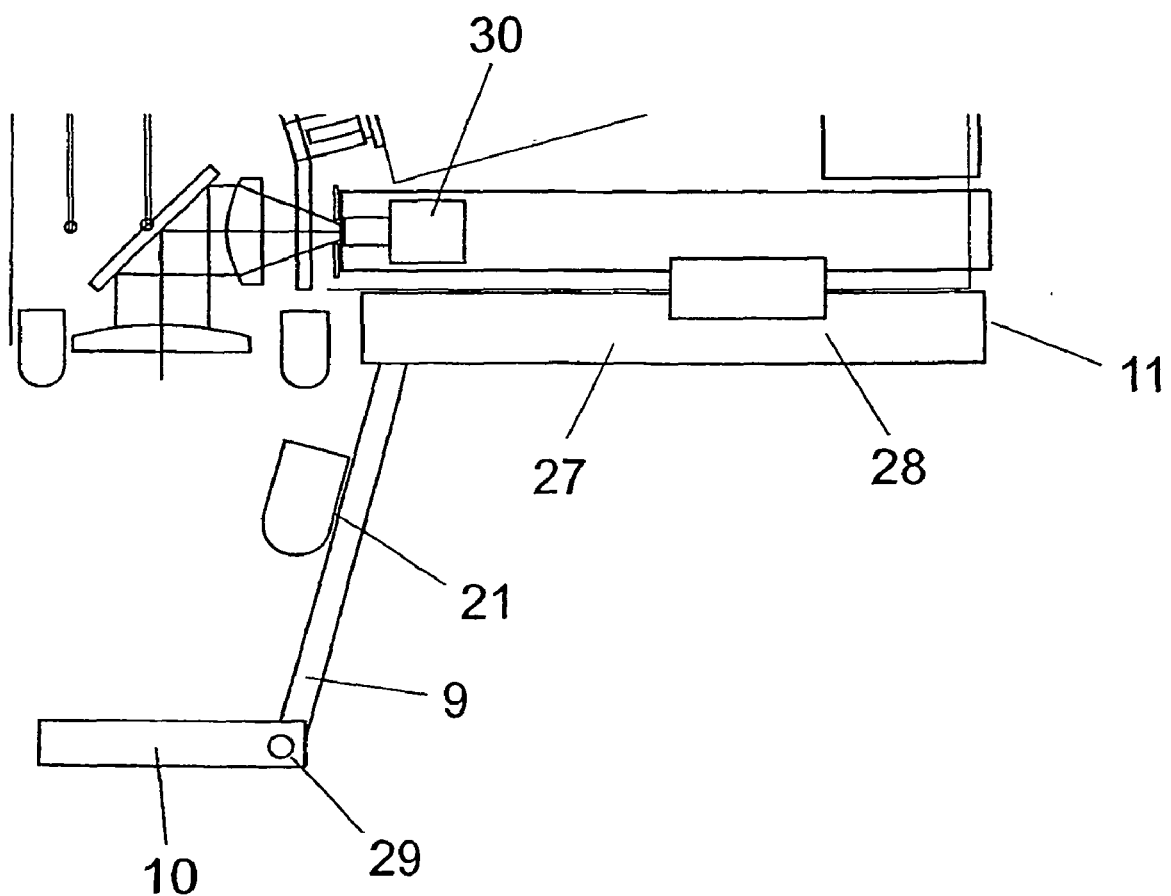
FIG. 11 shows the lower part of a handpiece having an attachment part attached thereto.

FIG. 11 shows the lower part of a handpiece having an attachment part 27 attached thereto. The attachment part 27 comprises means for supplying power to the handpiece and the attachment part 27 is provided with an electrical connection 28 for providing electrical power or signals to the handpiece via the attachment part 27. A distance piece 9 is mounted on the attachment part 27 and provided with a cooling member 10 for cooling the skin at the target area. The cooling member 10 has a temperature sensor 29 for measuring the temperature of the skin at the target area. In case the temperature of the target area raises to unacceptable values, the cooling may be increased, a warning signal may be sent to the user, or the treatment may automatically be interrupted in order to ensure that no damage is caused to the skin.

The attachment part 27 is also provided means for providing a cooling fluid, such as a cooling input 11, which is adapted to receive a cooling fluid. The cooling fluid is subsequently conveyed from the cooling input 11 via the attachment part 27 and the distance piece 9 to the cooling member 10. There the cooling fluid is used for cooling the skin at the target area. An illumination source 21 for illuminating the target area is mounted on the distance piece 9.

The attachment part 27 is mounted on the handpiece by means of a 'snap-on' system, i.e. it is easily attached or detached, and it is therefore very easy to exchange the attachment part 27. Thus, it is very easy to provide desired connections (e.g. cooling, electrical, optical etc.) to the handpiece, or to provide a distance piece 9 of a desired size and shape, or any other desired functionality of the attachment part 27 to the handpiece. Therefore, the easily attachable/detachable attachment part 27 provides a very flexible system which may also easily be adapted to future needs which are not yet defined.

Furthermore, a built-in light source 30 is provided in the handpiece for emission of the first light beam.

The invention claimed is:

1. A handpiece comprising:
    means for receiving a first light beam emitted from a first light source, the first light beam being emitted along a first beam path,
    at least two components,
    a selector device comprising the least two components and being movable between at least two positions, each position corresponding to a component being positioned in the first beam path,
    means for moving the selector device between said at least two positions, thereby positioning a selected component in a beam path of the first light beam, the selected component providing one or more functions,
    wherein the selector device comprises an elongated plate, and wherein the means for moving the selector device comprises means for moving the plate at least substantially linearly along a longitudinal axis of the elongated plate and wherein the at least two components are arranged along a longitudinal axis of the plate, and wherein a specific component is selected when a portion of the elongated plate comprising that component is moved linearly into the first beam path,
    wherein said means for moving being adapted to perform the movement of the selector device between said at least two positions with a position time smaller than 500 ms.

2. A handpiece according to claim 1, wherein the selected component provide a functionality selected from the group consisting of sensing, emitting a third light beam, emitting no light beam, and emitting a second light beam in response to the first light beam being incident on the selected component.

3. A handpiece according to claim 1, wherein the first light source comprises a laser device.

4. A handpiece according to claim 1, wherein at least one of the at least two components is a sensor providing information about a target area.

5. A handpiece according to claim 4, wherein the information provided comprises information about tissue parameters.

6. A handpiece according to claim 5, wherein the tissue parameters are selected from a group consisting of color, temperature, texture, elasticity, size, shape, reflectivity, and scattering properties.

7. A handpiece according to claim 5, wherein the information from the sensor is displayed on a display and wherein the displayed information comprises a map of the tissue parameters.

8. A handpiece according to claim 7, further comprising image processing means for processing the map for enhancement of selected tissue conditions.

9. A handpiece according to claim 7, further comprising user interface means for user selection of specific mapped tissue areas for treatment.

10. A handpiece according to claim 1, wherein at least one of the at least two components is a sensor for measuring the power of the first light beam.

11. A handpiece according to claim 1, wherein at least one of the at least two components provides a shutter function.

12. A handpiece according to claim 11, wherein the shutter is adapted to be operated on the basis of an output produced by a sensor measuring characteristics of the first light beam.

13. A handpiece according to claim 1, further comprising at least one second light source for providing illumination of a target area.

14. A handpiece according to claim 13, wherein the at least one second light source comprises a light source that is one of the at least two components.

15. A handpiece according to claim 1, further comprising a built-in light source for producing a treating light beam to be directed onto a target area.

16. A handpiece according to claim 15, wherein the treating light beam produced by the built-in light source is a highly focused light beam.

17. A handpiece according to claim 15, wherein the first light beam emitted from the first light source has a first wavelength and the treating light beam emitted from the built-in light source has a second wavelength, and wherein the first wavelength is different from the second wavelength.

18. A handpiece according to claim 1, further comprising a graphical display mounted on an upper surface of the handpiece.

19. A handpiece according to claim 18, wherein the display is adapted to display information in a user specified direction.

20. A handpiece according to claim 1, wherein the selected component provides a functionality selected from the group consisting of sensing, emitting a third light beam, and emitting no light beam.

21. A handpiece according to claim 1, wherein the component comprises a reflective mirror, a prism, a diffractive optical element, a sensor, a detector, a light source, a shutter, a non-linear medium, a diaphragm, and/or a collimator.

22. A handpiece according to claim 21, wherein the component further comprises a filter.

* * * * *

UNITED STATES PATENT AND TRADEMARK OFFICE
CERTIFICATE OF CORRECTION

| | | |
|---|---|---|
| PATENT NO. | : 8,092,447 B2 | Page 1 of 1 |
| APPLICATION NO. | : 10/521030 | |
| DATED | : January 10, 2012 | |
| INVENTOR(S) | : Casper Dolleris | |

It is certified that error appears in the above-identified patent and that said Letters Patent is hereby corrected as shown below:

Col. 7, line 38: "or drcular" should read --or circular--

Signed and Sealed this
Eighteenth Day of September, 2012

David J. Kappos
*Director of the United States Patent and Trademark Office*